United States Patent [19]
Galanakis

[11] Patent Number: 5,185,001
[45] Date of Patent: Feb. 9, 1993

[54] METHOD OF PREPARING AUTOLOGOUS PLASMA FIBRIN AND APPLICATION APPARATUS THEREFOR

[75] Inventor: Dennis K. Galanakis, Stony Brook, N.Y.

[73] Assignee: The Research Foundation of State University of New York, Albany, N.Y.

[21] Appl. No.: 467,143

[22] Filed: Jan. 18, 1990

[51] Int. Cl.$^5$ .............................................. A61M 5/00
[52] U.S. Cl. ...................................... 604/5; 604/191; 604/88; 604/201
[58] Field of Search .......... 604/88, 148, 191, 200-201, 604/411-414, 4-6; 424/101; 514/76

[56]  References Cited

U.S. PATENT DOCUMENTS

| | | | |
|---|---|---|---|
| 3,874,384 | 4/1975 | Deindoerfer et al. | 604/408 |
| 4,020,831 | 5/1977 | Alder | 604/403 |
| 4,359,049 | 11/1982 | Redl et al. | 604/191 X |
| 4,610,880 | 9/1986 | Giles et al. | 514/786 X |
| 4,735,616 | 4/1988 | Eibl et al. | 604/191 |
| 4,874,368 | 10/1989 | Miller et al. | 604/191 X |
| 4,902,281 | 2/1990 | Avoy | 604/88 X |
| 4,950,224 | 8/1990 | Gorosch et al. | 604/4 |
| 4,978,336 | 12/1990 | Capozzi et al. | 604/191 X |
| 4,979,942 | 12/1990 | Wolf et al. | 604/191 X |
| 5,030,125 | 7/1991 | Morse et al. | 604/410 |

OTHER PUBLICATIONS

"An Anaphylactic Reaction to Fibrin Glue", Anesthesiology and Analgesia, Milde, L. N., vol. 69, pp. 684-686, 1989.

"Autologous Fibrin For Blepharaplasty Incisions", JAMA, Mandel, M. A., vol. 262, No. 23, pp. 3271-3272, Dec. 15, 1989.

"Preparation Of Fibrin Glue From Single-Donor Fresh-Frozen Plasma", Surgery, Dresdale, A. et al., vol. 97, No. 6, pp. 750-754, Jun., 1985.

"Intraoperative Procurement And Utilization of Autologous Fibrin Glue", Abstract, Chest, vol. 96, No. 2, p. 129S, Aug., 1989, Honig, M. P., et al.

Primary Examiner—Robert A. Hafer
Assistant Examiner—Kerry Owens
Attorney, Agent, or Firm—Hoffmann & Baron

[57]  ABSTRACT

A method of preparing autologous plasma fibrin perioperatively to induce local hemostasis is disclosed. The autologous plasma fibrin is thereafter simultaneously expelled onto a treatment site along with a physiologically acceptable thrombin solution to effect hemostasis at the site. An apparatus for simultaneously expelling the contents of vessels which separately contain the autologous plasma fibrin and thrombin solutions, respectively, is also disclosed. A kit for obtaining a sample of blood, extracting plasma fibrin therefrom, as well as all necessary syringes, needles, reagents, and the inventive apparatus is also disclosed.

25 Claims, 6 Drawing Sheets

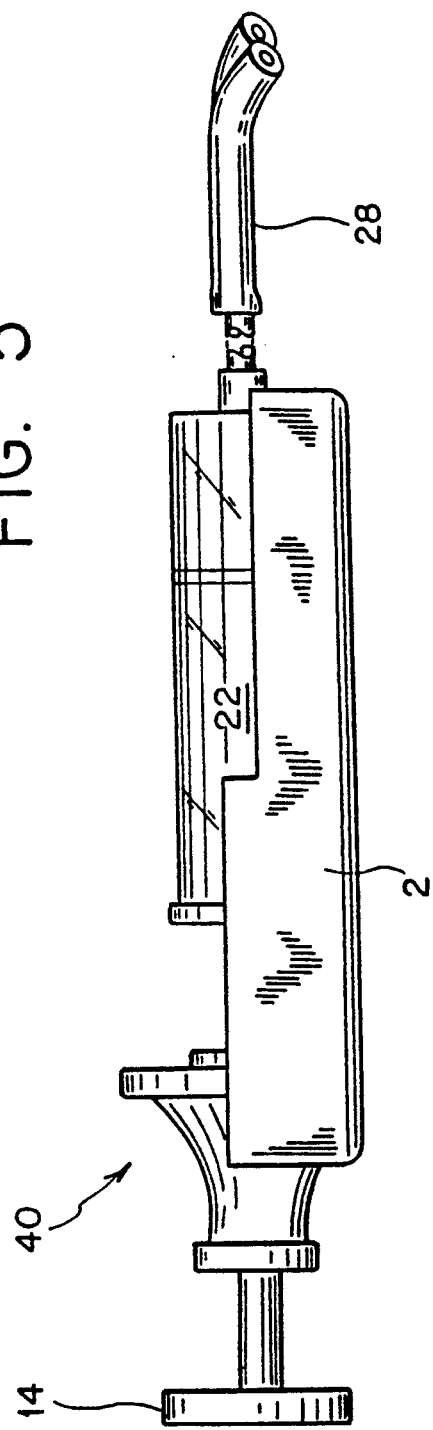

METHOD OF PREPARING AUTOLOGOUS PLASMA FIBRIN AND APPLICATION APPARATUS THEREFOR

BACKGROUND OF THE INVENTION

The present invention relates to a method of inducing hemostasis in mammals, and, in particular to providing a method for applying a highly effective hemostatic agent at a desired treatment site with a plasma fibrin and thrombin composition. The invention further relates to a kit suitable for the preparation and application of the hemostatic agent prepared in accordance with the present invention.

Plasma refers to the liquid portion of the blood in which the particulate components thereof are normally present. The chief components of plasma are proteins, anions, and cations. The proteins include albumin and globulins. Anions are chiefly chloride and bicarbonate, while cations are largely sodium, potassium, calcium and magnesium. Blood plasma also circulates immunoglobulins and several of the essential components for blood clot formation described in further detail below.

The clotting of blood as a part of the body's natural response to an injury or trauma is part of the natural phenomenon of hemostasis. Blood clot formation derives from a series of events called the coagulation cascade in which the final steps involve the formation of the enzyme thrombin. Thrombin converts circulating fibrinogen into fibrin, a mesh-like structure which forms the insoluble structure of the blood clot.

Normally, thrombin does not exist in the active state within the blood circulation system but rather in the form of an inactive precursor, prothrombin. Thrombin is activated, however, through one of two mechanisms commonly referred to as the extrinsic and intrinsic pathways. The pathways are schematically represented in FIG. 1.

The intrinsic pathway activates thrombin when blood contacts glass outside the body, as in a test tube or other negatively charged surfaces and is not pertinent to the subject of the present invention. The extrinsic pathway, on the other hand, activates thrombin when blood comes in contact with injured tissues which produce tissue thromboplastin. The interactions of tissue thromboplastin with naturally present calcium ions and several plasma proteins lead to the conversion of prothrombin to thrombin.

As a part of hemostasis, clot formation is often a life-saving process in response to trauma and serves to arrest the flow of blood from severed vasculature. In addition, it is often desirable to initiate or enhance the body's natural hemostatic process. For example, after severe trauma, a victim may require supplemental assistance in stopping bleeding or hemorrhage caused by the trauma. Alternatively, a physician may wish to initiate and/or enhance wound closure after surgery.

The use of exogenous thrombin as a clot-enhancing or hemostatic agent is known in the art. Thrombin of bovine origin is useful in surgery or emergency situations for local application in the control of minor oozing. Thrombin is applied topically as a powder or in a solution at the site of the wound.

The use of thrombin as a single agent for inducing clotting and hemostasis, however, is limited to minor clots or injuries. In more extensive bleeding or in hemorrhage, it is necessary to employ a matrix to hold the thrombin at the desired location and to provide a structure for clot formation. Matrix materials known in the art include fibrin foam-like compositions and gelatinous sponges. Even with such matrix materials, thrombin is generally regarded as ineffective for inducing coagulation and hemostasis on arterial bleeding.

An alternative approach to the use of thrombin as an adjunct in inducing coagulation involves the application of thrombin along with fractionated plasma at the wound site.

Fractionated plasma is obtained from either autologous or nonautologous blood sources at least several hours in advance of need, usually a day before, and is frozen, cryoprecipitated and then thawed before being combined with thrombin at the site of need. Recent concerns with the use of blood products obtained from sources foreign to the patient have severely limited the use of nonautologous plasma due to the possibility of disease transmission in spite of extensive precautions.

The use of fractionated plasma as a thrombin adjunct in promotion of therapeutic clotting is therefore significantly hampered by the methods of the prior art since the plasma must be obtained several hours and usually a day prior to its use. The problems are magnified when emergency situations arise and the several hour time lag for plasma fractionation is unavailable or otherwise impracticable.

The aforementioned approaches and techniques for inducing therapeutic clotting and coagulation therefore all fall short of providing a method for treating undesired bleeding in mammals. Thrombin alone is often insufficient and needs supplementation to be effective. Thrombin enhanced with cryoprecipitated fibrin obtained from plasma has several drawbacks. The most significant drawback to date has been the lengthy time delay between the drawing of blood and extraction of the plasma fibrin before end use. Nonautologous sources of blood plasma are now largely avoided since they expose the patient to the risk of contacting serious diseases transmitted by foreign blood products.

Accordingly, there exists a need for providing an improved method for treating undesired bleeding by inducing coagulation with thrombin and a plasma fibrin composition. There is also a need for providing the plasma fibrin for use with thrombin to induce clotting in a much more rapid manner than the prior art allows.

It is therefore an object of the present invention to provide a new and improved method for effecting therapeutic hemostasis and coagulation.

It is a further object of the present invention to provide such a method using whole plasma fibrin.

A still further object of the present invention is to provide such a method using autologous whole plasma fibrin which is obtained perioperatively.

Yet another object of the present invention is to provide a kit for the perioperative preparation of whole plasma fibrin and a thrombin solution for application on selected treatment sites.

A still further object of the present invention is to provide a means for applying whole plasma fibrin and thrombin solutions contained in separate vessels so that the whole plasma fibrin and thrombin initiate contact with each other at the site of the wound to effect coagulation.

Other objects and advantages will become apparent to those skilled in the art from a consideration of the ensuing description.

SUMMARY OF THE INVENTION

In accordance with the present invention, there is provided a method of treating with autologous mammalian plasma fibrin to provide therapeutic coagulation of blood. Autologous plasma fibrin is obtained from blood taken from the patient in whom the therapeutic coagulation is sought. The present invention allows the clinician to obtain the plasma from the blood sample perioperatively and without the several hour delay required by the prior art methods of cryoprecipitation.

The present invention is further directed to a kit useful in the preparation and extraction of the plasma from the autologous blood sample as well as the preparation of a thrombin solution and subsequent application of both components on the treatment site. The kit contains a means for obtaining a sample of blood, structure for stabilizing the obtaining means, means for extracting whole plasma from the obtaining means, means for providing a thrombin solution in a physically acceptable vehicle and apparatus for simultaneously expelling the solutions of the thrombin and plasma simultaneously at the desired site of treatment. The apparatus releasably retains a vessel containing plasma and a vessel containing thrombin and is capable of simultaneously expelling the respective contents of the vessels retained within the apparatus.

As a result of the present invention it is now possible to effect local hemostasis with an autologous plasma fibrin without the heretofore unavoidable cryoprecipitation time delays in plasma harvesting. The perioperative harvest of the plasma component of the blood sample obtained from the patient prior to need has tremendous advantages over the methods of the prior art. Extensive time delays are eliminated. Disease transmission caused by using nonautologous blood supplies is eliminated. Further, allergic reactions due to foreign substances being introduced into the body of the mammal at the treatment site are significantly reduced.

For a better understanding of the present invention, together with other and further objects, reference is made to the following description, taken in conjunction with the accompanying examples, and drawings and its scope will be pointed out in the appended claims.

BRIEF DESCRIPTION OF THE DRAWINGS

FIG. 5 is an elevated side view of the assembled delivery apparatus of FIG. 4.

DESCRIPTION OF THE PREFERRED EMBODIMENTS

Figure 1:
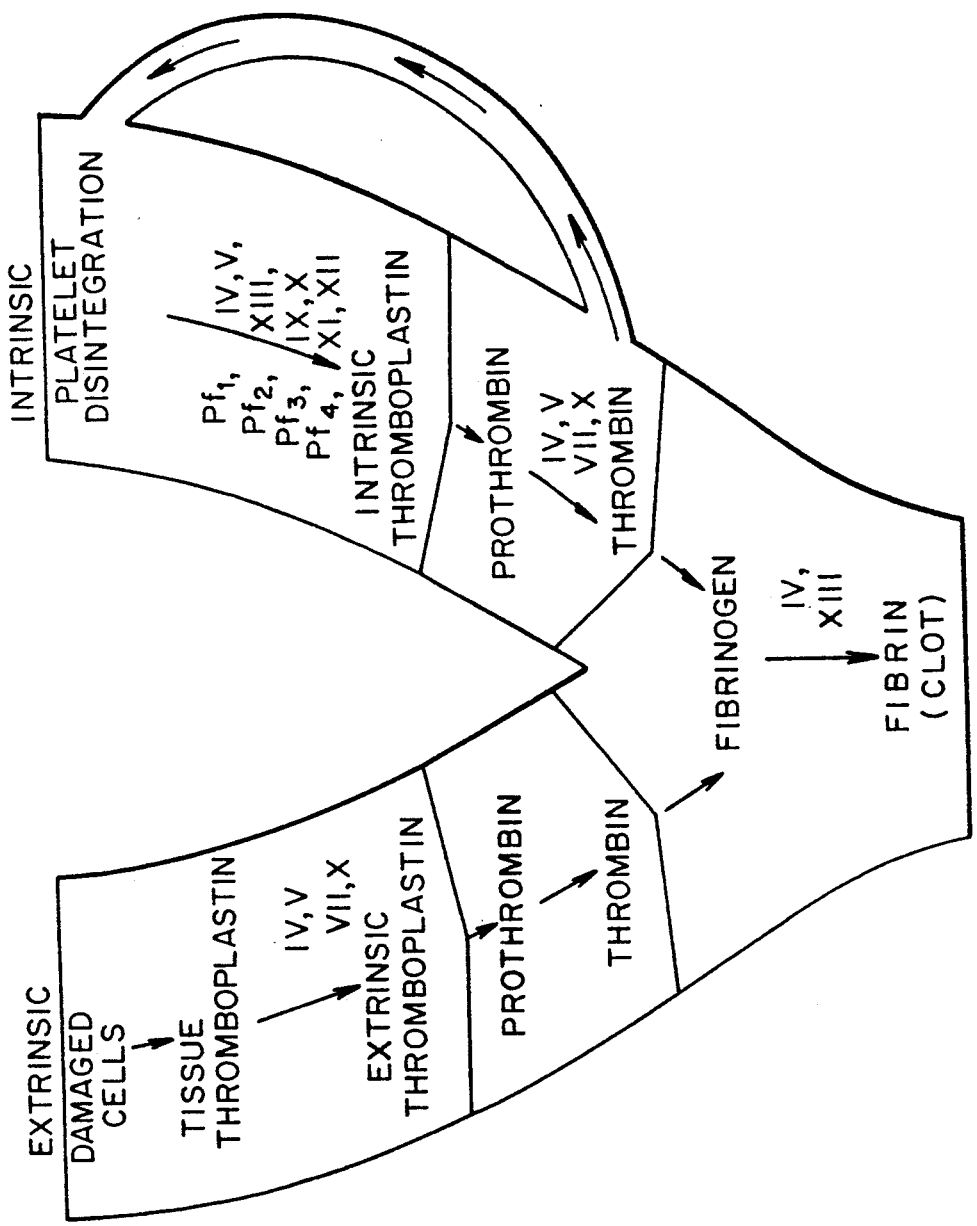
FIG. 1 is a schematic representation of the coagulation cascade showing both the extrinsic and intrinsic pathways and their convergence to a common pathway resulting in clot formation.

The method of the present invention is characterized by its capacity to allow clinicians to perioperatively obtain autologous plasma from mammals requiring therapeutic hemostasis. The method of the present invention is further characterized by its use of plasma fibrin without need for the time-consuming process of cryoprecipitation. It has been surprisingly found that the disadvantages associated with topical application of surface coagulants such as fibrin which imitates the final phases of blood clotting mechanisms can be overcome by using the novel method of the present invention. The method of the present invention is further enhanced by the kit and apparatus described herein for the preparation and application of the ingredients necessary for fibrin coagulation, more specifically, autologous plasma containing fibrinogen and separately, thrombin.

Topical application of fibrin for the purposes of initiating hemostasis as a surface coagulant has resulted in the medical community referring to such use of fibrin as that of a "glue". For the purposes of the present invention "fibrin glue" will be used in a manner consistent with the understanding of those skilled in the art.

In a preferred embodiment, a sufficient quantity of blood is obtained by hypodermic syringe from a mammal who will require therapeutic hemostasis. The syringe containing the blood is then inverted and immobilized. Substantially immediately thereafter, the plasma portion of the blood is harvested therefrom without resorting to cryoprecipitation. The harvested plasma contains the fibrin precursor fibrinogen, which, when combined with a solution containing the fibrin enzyme activator, thrombin, at the treatment site according to the method of the present invention provides therapeutic hemostasis of the circulating blood. Though not wishing to be bound by any particular method, the surface coagulation of blood at the treatment site is believed to be achieved by the naturally known hemostasis blood clotting mechanism factors which have been placed at the treatment site by the inventive method herein.

In order to prepare the autologous plasma component, it is necessary to first obtain a sample of the patient's blood. As a result of the present invention, it is now possible to obtain the sample of blood at a time at or near final use. The amount of blood necessary to be drawn prior to plasma harvesting is dependent upon the size of the treatment site area. It has been found, for example, that a 50 ml sample of blood will provide an adequate amount of plasma for the needed coagulation of thoracic surgery incision sites. Once the sample of blood has been obtained from the patient requiring therapeutic coagulation, the vessel containing the blood is sealed, inverted and immobilized to effect plasma separation from the blood. It has been found that the addition of a small amount of an anticoagulant such as trisodium citrate effectively reduces the coagulation of the whole blood while in the syringe before plasma is separated. Once the blood has been immobilized for between about one-half to one and one-half hours, the plasma portion of the blood which has now separated is withdrawn and placed in a second syringe.

Separately, a physiologically acceptable solution containing thrombin is prepared. In addition to the thrombin solution, there is added a sufficient amount of a physiologically acceptable form of calcium. The calcium source is added to the thrombin so that coagulation is enhanced. The normal hemostasis method of coagulation relies upon calcium ions present within the body to assist in thrombin's conversion of circulating fibrinogen to stable fibrin.

When the clinician is ready to effect surface coagulation using the method of the present invention, the contents of the syringe containing the plasma as well as the syringe containing the above-mentioned thrombin are expelled from their respective syringes, contacting each other at the site of treatment. The contacting of the solution containing the thrombin and calcium along with that of the plasma imitates the naturally occurring hemostasis blood clotting mechanism's final steps. In particular, the fibrinogen contained within the plasma in the presence of thrombin and calcium is converted to the mesh-like clot of fibrin at the site of wound.

There is also provided a kit useful in practicing the method of treatment according to the present invention. Surface coagulation of blood at the desired treatment site may be carried out by using the kit prepared in accordance with the present invention. The kit contains all of the apparatus and reagents needed to effectively implement hemostasis according to the method of the present invention. An example of a kit prepared in accordance thereto is illustratively shown in FIG. 2.

Figure 2:
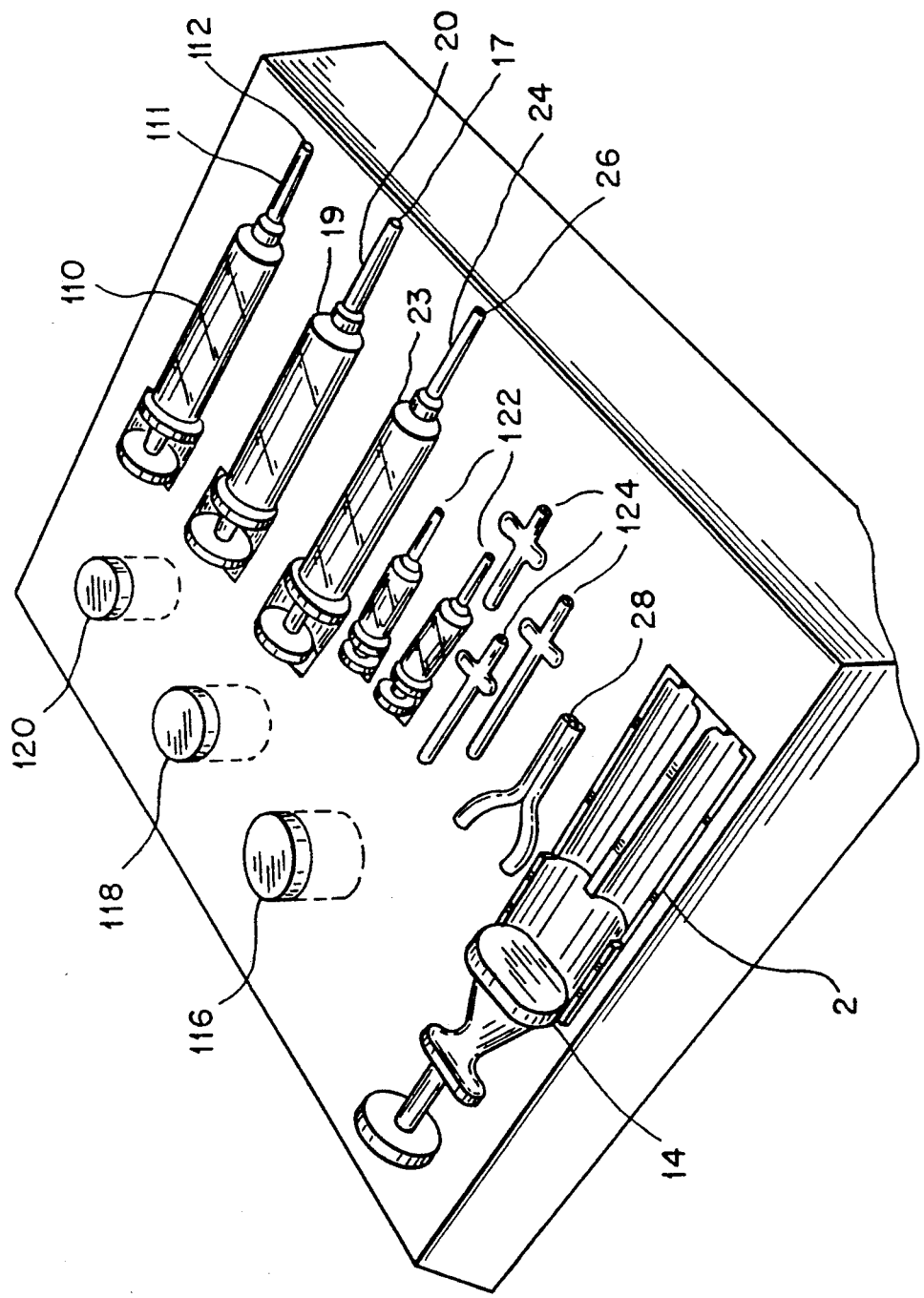
FIG. 2 is a perspective view of one embodiment of the kit provided herein for effecting the unique method of the present invention.

Referring now to FIG. 2, there is shown a hypodermic syringe 110 and needle 111 for obtaining a sample of blood from the mammal requiring treatment. The kit further provides syringes 19, 23, with needles 20, 24 attached thereto along with sterile protection covers 17, 26, 112 covering the needles. Also included is a vial of thrombin solution 116, a vial of calcium chloride solution 118 and a vial of an anticoagulant 120 such as trisodium citrate which is added to the sample of blood in the syringe before effecting plasma separation and harvesting of the desired fibrin. In addition, the kit provides all necessary sterile transfer syringes 122 and needles 124 for harvesting of the plasma fibrin from the blood sample as well as for withdrawing the thrombin solution and calcium chloride solution from their respective vials and into delivery syringes 19, 23. The kit further provides a delivery apparatus housing 2 and plunger 14 which retain the syringes 19, 23 containing the harvested plasma and thrombin solution containing calcium chloride, respectively, on the apparatus housing and simultaneously expel the contents therein. A bifurcated connecting element 28 adapted to cooperatively fit over the needles 20 and 24 after syringes 19, 23 have been placed in the housing 2.

Figure 3:
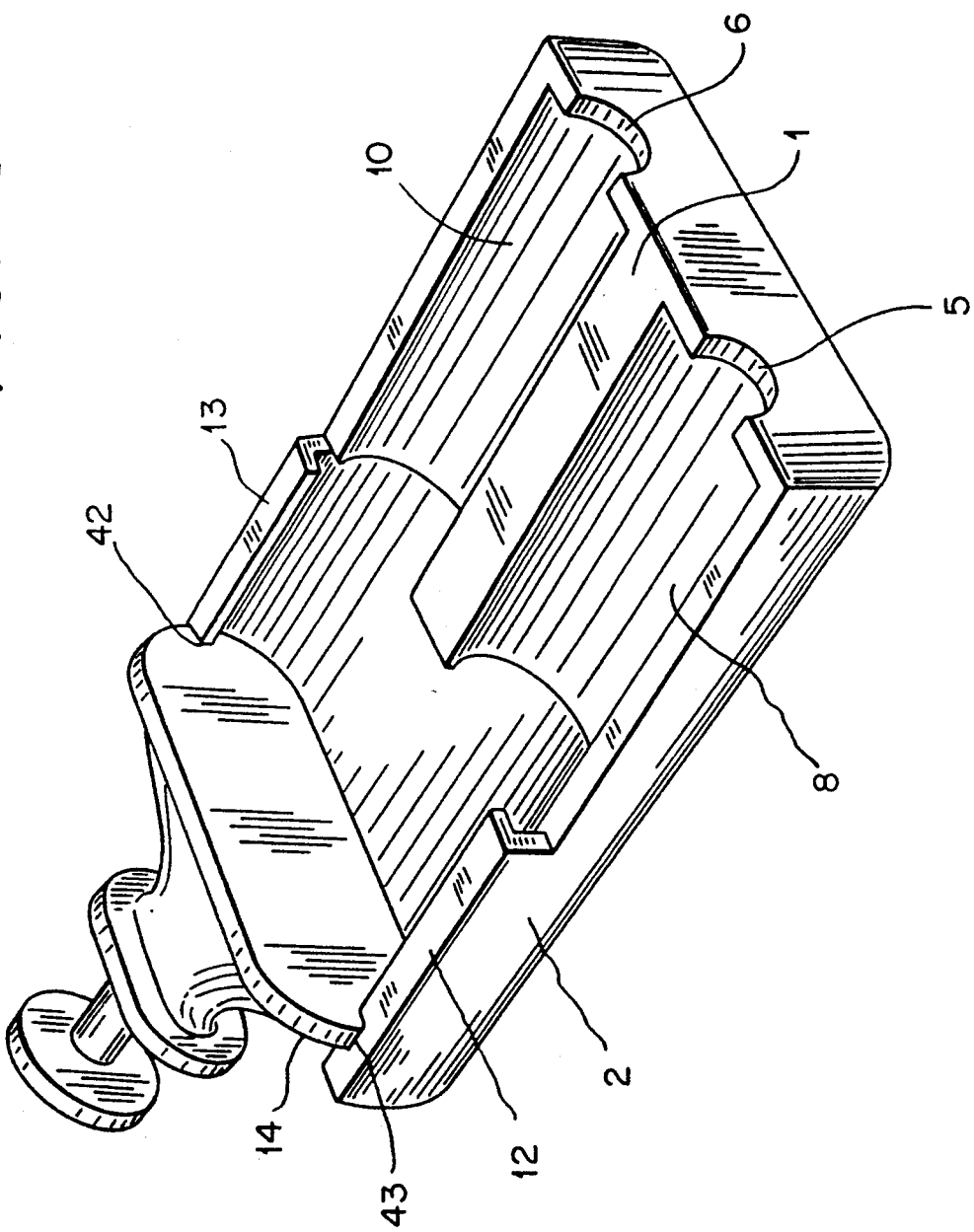
FIG. 3 is a perspective view of the delivery apparatus housing and expulsion means.

Referring now to FIG. 3, there is perspectively shown a delivery apparatus housing 2 having a plunger 14 operatively attached thereto by first and second guide members 12 and 13 provided along the outer edges of the housing. As shown herein, plunger 14 is formed with receiving channels 42 and 43 for sliding along guide members 12 and 13. The upper surface 1 of said housing is adapted for securing at least two vessels thereon. Securing may be accomplished by providing contoured recesses 8, 10 on surface 1 along with tapered ends 5 and 6 distal to the plunger 14.

Figure 4:
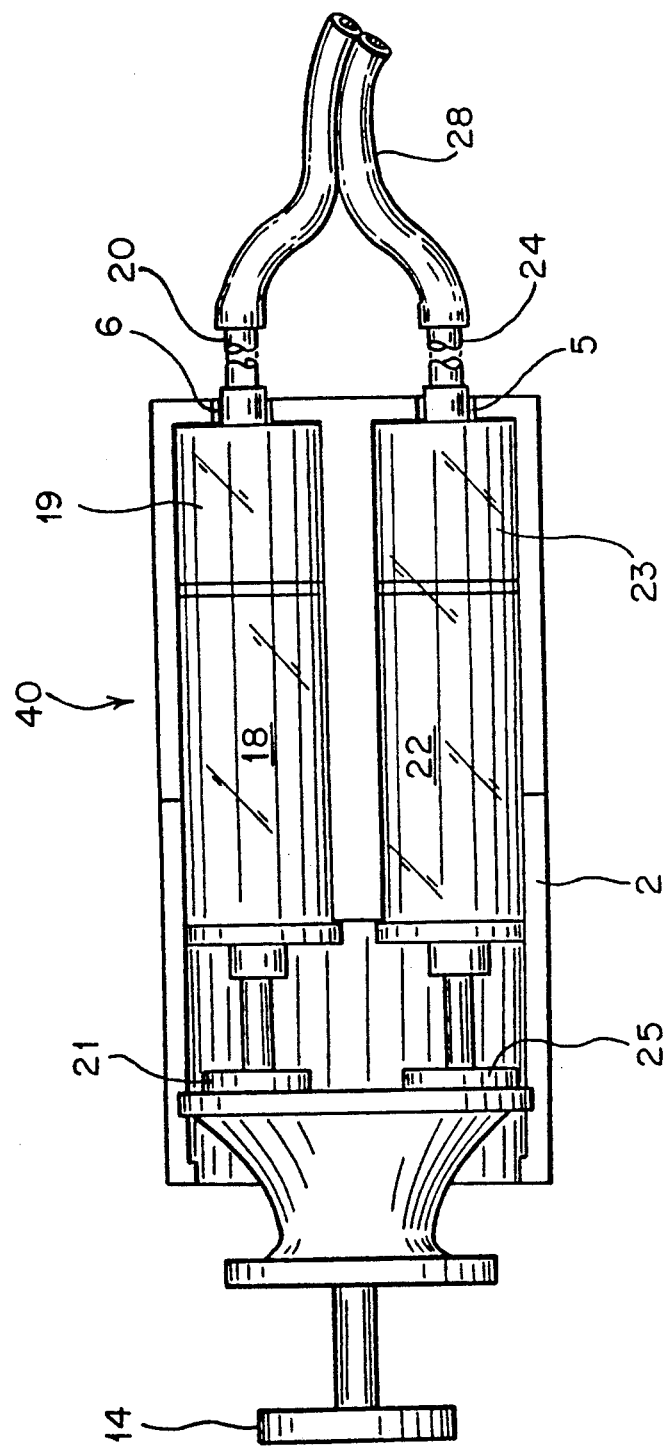
FIG. 4 is a plan view of the assembled delivery apparatus of FIG. 3.

Referring now to FIGS. 4-5, there is perspectively shown an assembled delivery apparatus 40. A device 18 for containing whole plasma is depicted as a syringe 19, a needle 20 and plunger 21. Similarly, a device 22 for providing a physiologically acceptable thrombin solution is shown as a syringe 23, needle 24, and plunger 25. Both devices are releasably secured to the housing 2 by friction fit in a pair of contoured recesses 8, 10 having tapered ends 5, 6.

The assembled syringes 18, 22 may be of various sizes to provide the required volumes of plasma and thrombin. The syringes preferably have protective contamination isolating covers 17, 26 when needles 20, 24 are not in place.

The apparatus for simultaneously expelling the whole plasma and thrombin solution from their respective vessels includes the plunger 14 operatively joined to housing 2. Once placed therein, the plunger can be easily moved with one hand to simultaneously expel the contents of the plasma syringe 18 and the thrombin syringe 22.

Also shown is a bifurcated connecting element 28 which may be made from any suitable tubing material or adapted from a double lumen catheter. The bifurcated connecting element is shown in more detail in FIGS. 6a and 6b.

Figure 6A:
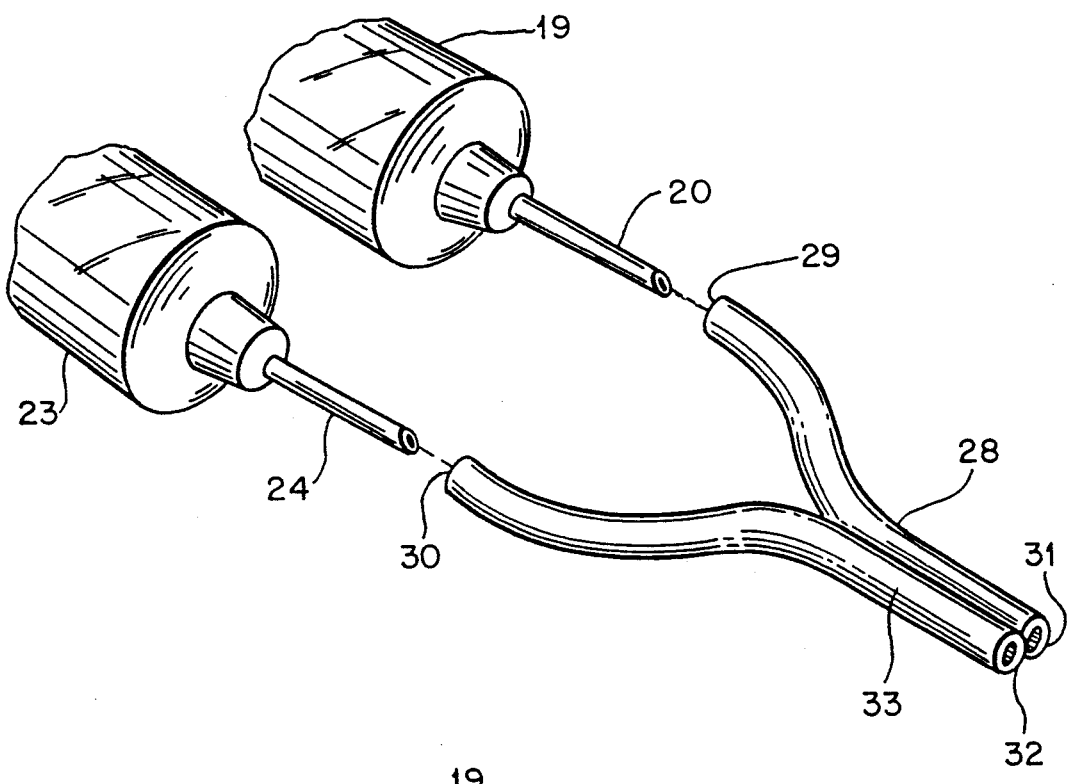
FIG. 6a is an exploded perspective view of syringe needles and a bifurcated connecting element.
Figure 6B:
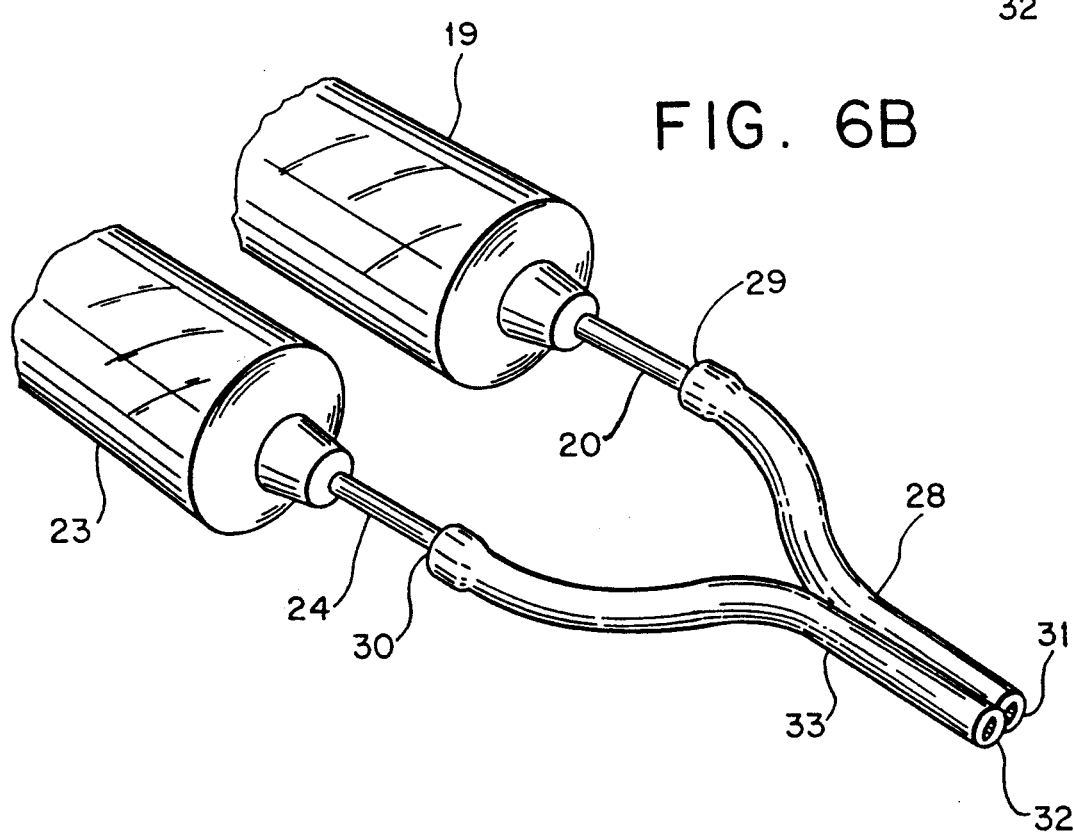
FIG. 6b is a perspective view of the bifurcated connecting element joined to the syringe needles.

Referring now to FIGS. 6a and 6b, the bifurcated connecting element 28 is shown having first and second receiving ports. The first receiving port 29 is joined to needle 20, the second receiving port 30 is joined to needle 24 when the needles are held in the housing 2. The bifurcated connecting element 28 also has tubing 33 to allow fluid transmission from the receiving ports to a first exit port 31 and a second exit port 32 which are shown in contact with each other due to the tapered tubing 33 s that tubes intimately contact one another at the exit ports thus allowing the fluids thrombin and plasma to be expelled at the site of treatment and mixed thereon.

EXAMPLE

The following example serves to provide further appreciation of the invention but is not meant in any way to restrict the effective scope of the invention.

Example I

A 50 ml sample of whole blood was withdrawn via syringe from a patient shortly before surgery and citrated in a manner known in the art so that the blood sample contained approximately 0.3% citrate within the blood sample. The citrated blood was thereafter sealed in the syringe, inverted and immobilized to effect plasma separation. After a sufficient time of immobilization, for example, usually between one-half to one and one-half hours, sufficient plasma, for example 20 ml, is available to be harvested from the citrated blood. The plasma so obtained is thereafter placed in a separate syringe.

Separately, a second syringe is prepared to contain thrombin which is available, for example, 20 ml in a 50 U/ml concentration, and along with calcium chloride. It has been found, for example, that about 0.1 ml of a 10% calcium chloride solution provides sufficient calcium for the coagulation of the above-mentioned thrombin and plasma according to the present invention.

To effect surface coagulation at the treatment site, similar amounts of the plasma and thrombin solution containing calcium chloride were expelled at similar rates from their respective syringes in close proximity to each other, effectively mixing the two contents on the surface of the treatment area. Coagulation of the blood was observed shortly thereafter.

What is claimed is:

1. A method of treating with autologous mammalian plasma fibrin to affect hemostasis, comprising the steps of:
   (a) obtaining a sample of blood from said mammal;
   (b) substantially immediately separating the whole plasma from said blood obtained in step (a); and (c) contacting said whole plasma resulting from step (b) with thrombin in a physiologically acceptable solution at a rate and in a volume at the site of treatment to provide fibrin coagulation at said site.

2. The method of claim 1, wherein said blood is obtained perioperatively.

3. The method of claim 2, wherein said blood is obtained between about one-half and about one and one-half hours prior to treatment.

4. The method of claim 1, wherein said separating comprises immobilizing a vessel containing said blood in the presence of an anticoagulant.

5. The method of claim 4, wherein said anticoagulant is selected from the group consisting of trisodium citrate, and other citrate salts.

6. The method of claim 4, wherein said vessel is stabilized for a time period of from about 30 minutes to about 90 minutes.

7. The method of claim 4, wherein said vessel is stabilized for a time period of from about 45 minutes to about 65 minutes.

8. The method of claim 1, wherein said separation is conducted at room temperature.

9. The method of claim 1, wherein said thrombin solution is prepared by premixing with a calcium chloride source.

10. The method of claim 1, wherein said contacting is effected by simultaneous expelling of said plasma and said thrombin solution at said treatment site.

11. The method of claim 10, wherein thrombin solution is contacted with said plasma at a ratio of from about 0.5 to about 1 of thrombin to about 1 to about 2 of plasma.

12. The method of claim 10, wherein thrombin solution is contacted with said plasma at a ratio of from about 1 of thrombin to about 1 of plasma.

13. A kit for treatment with autologous mammalian plasma fibrin to effect hemostasis, comprising:
   (a) means for obtaining a sample of blood from said mammal, said means including structure for effecting plasma separation of said blood, said structure having at least two open ends located opposite each other;
   (b) means for extracting whole plasma from said obtaining means, said plasma extracting means including structure having at least two open ends located opposite each other;
   (c) means for providing a physiologically acceptable thrombin solution, said means including structure having at least two open ends distally located, said plasma extracting means and said means for providing a physiologically acceptable thrombin solution having substantially equal cross-sectional area;
   (d) means for simultaneously expelling said whole plasma from said extracting means and said thrombin solution from said means for providing locally at the site of treatment.

14. A kit of claim 13, wherein said means for obtaining a sample of blood comprises a syringe and a removable needle, said syringe having a releasable connection for said needle and sealing means for isolating the contents thereof from contamination.

15. The syringe of claim 14, which has been provided with an anticoagulant.

16. The syringe of claim 15, wherein said anticoagulant is chosen from the group consisting of trisodium citrate, other citrate salts.

17. The syringe of claim 15, wherein said anticoagulant is present in an amount of from about 0.25% to about 0.5% of said blood.

18. The kit of claim 13, wherein said means for extracting whole blood plasma is a syringe and needle adapted to be cooperatively arranged in said means for expelling plasma and thrombin.

19. The kit of claim 18, further comprising a transfer syringe for withdrawing plasma from said means for obtaining and injecting into a prearranged syringe in said means for expelling.

20. The kit of claim 13, wherein said means for providing is a syringe containing thrombin.

21. The kit of claim 20, wherein said means for providing contains a predetermined amount of calcium chloride.

22. The kit of claim 21, wherein said calcium chloride is present in an amount of from about 0.02 to about 0.04% of said thrombin.

23. The kit of claim 13, wherein said means for expelling includes housing for holding said means for extracting proximal to said means for providing for simultaneous expulsion of the contents of each,
   means for expulsion of said whole plasma from said extracting means substantially simultaneously,
   means for delivering said whole plasma and said thrombin to said treatment site substantially proximal to each other to effecting mixing said thrombin and said plasma thereat whereby fibrin coagulation is achieved.

24. The kit of claim 23, wherein said means for expulsion is a plunger.

25. The kit of claim 23, wherein said means for delivering said thrombin and said plasma to said treatment site is a double lumen catheter operatively connected to said means for extracting and said means for providing for fluid flow to said site of treatment.

* * * * *